(12) United States Patent
Lô

(10) Patent No.: US 6,514,716 B1
(45) Date of Patent: Feb. 4, 2003

(54) DETECTION OF THE END-POSITION SIALIC ACID GROUPS OF THE HUMAN TRANSFERRIN MOLECULE

(76) Inventor: Atou Lô, Goldregenweg 38, D-70565 Stuttgart (DE)

( * ) Notice: Subject to any disclaimer, the term of this patent is extended or adjusted under 35 U.S.C. 154(b) by 0 days.

(21) Appl. No.: 09/077,252

(22) PCT Filed: Nov. 21, 1996

(86) PCT No.: PCT/EP96/05141

§ 371 (c)(1),
(2), (4) Date: May 17, 2000

(87) PCT Pub. No.: WO97/19355

PCT Pub. Date: May 29, 1997

(30) Foreign Application Priority Data

Nov. 22, 1995  (DE) .......................................... 195 43 569

(51) Int. Cl.⁷ ...................... G01N 33/53; G01N 33/543; C12Q 1/28; C07K 16/00
(52) U.S. Cl. ...................... 435/7.92; 435/7.1; 435/7.94; 435/28; 435/975; 436/518; 436/536; 436/811; 436/827; 530/387.7; 530/388.25; 530/389.3; 530/391.1; 530/391.3; 530/396
(58) Field of Search ................................ 436/827, 518, 436/536, 811; 530/387.7, 388.25, 389.3, 396, 391.1, 391.3; 435/975, 7.92, 7.94, 28, 7.1

(56) References Cited

U.S. PATENT DOCUMENTS 6,048,704 A * 4/2000 Tilson ........................ 435/69.1
6,136,545 A * 10/2000 Hosel et al. .................. 435/7.1
6,168,928 B1 * 1/2001 Read et al. .................... 435/15

FOREIGN PATENT DOCUMENTS

WO         9306133    *  4/1993   .................. 33/545

OTHER PUBLICATIONS

Shibuya et al Archives Biochemistry and biophysics vol. 254 No. 1 Apr. 1987 pp. 1–8.*
Pekelharing Analytical Biochemistry 165 320–326 1987*
Schellenberg et al. Alcohol and alcoholism Suppl 1 pp. 615–620 (1987).*
Regoeczi et al alcoholism: Clinical and Experimental research vol. 8 No. 3 (1984).*
Heegaard et al Electrophoresis (1989) 10 836–840.*
Cerven et al Upsala J. Med. sci. 86: 39–53 (1981).*

* cited by examiner

Primary Examiner—Christopher L. Chin
Assistant Examiner—Kartic Padmanabhan
(74) Attorney, Agent, or Firm—Fulbright & Jaworski L.L.P.

(57) ABSTRACT

The subject matter of this invention is a method of determining terminal sialic acid residues in human transferrin according to a sandwich principle, which is characterized in that the sample fluid containing the human transferrin is incubated with a first receptor which binds specifically to human transferrin, the thus-formed complex is separated from the sample fluid and incubated with a second receptor which binds specifically to terminal sialic acid residues in human transferrin, the second receptor being bound or able to bind to a marker, and the complex made up of the first receptor, human transferrin and the second receptor is determined with the marker. According to one embodiment, the method of the invention allows the determination of sialic-acid-deficient human transferrin in body fluids.

17 Claims, 2 Drawing Sheets

DETECTION OF THE END-POSITION SIALIC ACID GROUPS OF THE HUMAN TRANSFERRIN MOLECULE

This is the National Stage Application of PCT/EP96/05141 filed Nov. 21, 1996 and published May 29, 1997.

BACKGROUND AND SUMMARY OF THE INVENTION

This invention relates to the determination of the terminal sialic acid residues in human transferrin. One embodiment of the invention relates to the quantification of terminal sialic acid residues in transferrin contained in samples of human body fluids, and in particular to an interpretation of changes in the chemical structure of transferrin such as are caused, for example, by regular and excessive alcohol consumption.

There are a number of indicators used in medicine to diagnose alcohol abuse or addiction. With the help of so-called "state markers", it is possible to estimate alcohol consumption, different markers serving to estimate consumption over a short period of time (eg, blood alcohol level) or over longer periods (in particular various hepatic enzymes). A detailed review of alcoholism and suitable markers is contained in M. Soyka (publisher, Biological Markers for Alcoholism, Chapman and Hall, (1995)).

An abnormal transferrin variant has proved to be a suitable marker with a relatively high degree of specificity. The scientific studies published so far have shown that this molecular modification takes the form of a lack or a reduction in the number of sialic acid residues in the transferrin molecule.

Human serum transferrin is a glycoprotein with a relative molecular weight of about 77,000 g/mol. It consists of a single peptide chain of 679 amino acids, to which two oligosaccharide chains consisting of N-acetyl glucosamine, mannose and galactose are attached. These carbohydrate chains have two to three antennae, to the ultimate unit of which (galactose) a sialic acid residue is bound.

Regular alcohol abuse impairs the mechanism by which sialic acid is transferred to transferrin, and as a consequence there are increased numbers of transferrin isomers with fewer than the usual four-to-six terminally bound sialic acid residues (desialicized transferrin, sialic-acid deficient transferrin, sialic deficient transferrin, SDT)

According to Jong et al. (1980), the most common tetra-sialotransferrin isomer (FIG. 1) is made up of:

- 4 terminal N-acetyl sialic acid residues, 4 galactose residues, 8 N-acetyl glucosamine residues and 6 mannose residues in each oligosaccharide side-chain of the transferrin molecule.

Methods described in the prior art are based mainly on the separation of differently glycosylated transferrin derivatives by way of their charge, eg, by way of isoelectric focusing or chromatographic techniques. Familiar methods include:

1. The isoelectric focusing method Electrophoretic separation of isotransferrins according to their isoelectric points (Pl 6.1–5.1). (Helena Stibler and Stefan Borg, Pharmacol. Biochem. Behav. 1980, 13, Suppl. 1, 47–51).
2. The chromatographic method by means of ion exchanger (Helena Stibler et al., Clinical and Experimental Research Sept./Oct. 1986, Vol. 10, No. Pages 535–543).
3. The HPLC method Saturation of the transferrin with an iron salt, followed by extraction on a column and subsequent densitometric determination. (Strahler et al., J. of Chromatography 266, 1983, 281–289).
4. Isocratic HPLC method Based on the separation of isotransferrins by means of cationic buffers. (Joustra Marius et al., Patent No. EP 0 172 217 B1), (HPLC techniques according to Jan Jeppson et al., Clin. Chemistry 39/10; 2115–2120 (1993).
5. Turbidimetric method of the company AXIS Likewise based on saturation of the isotransferrin by means of iron salt or a heterogeneous immunoassay with separation on a column followed by a turbidimetric measurement. (Patent: WO 99119983 A 911226).
6. The immunoenzymatic EIA method involving a Pharmacia conjugation Uses a monoclonal antibody after saturation of the isotransferrin with an iron salt and column separation (O. Märtenson et al.).
7. Pharmacia's RIA method: A chromatographic method using an ion exchanger after saturation of the isotransferrin with an iron salt and quantitative determination by means of radio-immunoassay.

A The above-mentioned methods, however, are not yet satisfactory for the user. The likelihood of false diagnoses and the very complicated and time-consuming test procedures are particularly problematical.

The prior art also describes a class of proteins or glycoproteins referred to as lectins, which bind to certain carbohydrate configurations and to glycoproteins which carry such carbohydrate configurations. On account of their specificity for certain carbohydrates, such lectins have been used, eg, for the blood-group-specific agglutination of erythrocytes.

The object of this invention was to provide a method allowing rapid and uncomplicated determination of terminal sialic acid residues in human transferrin.

This object is established according to the invention by a method of determining terminal sialic acid residues in human transferrin contained in a sample fluid, said method being based on a sandwich principle and being characterized in that the sample fluid is incubated with a first receptor which binds specifically to human transferrin, the thus-formed complex is separated from the sample fluid and incubated with a second receptor which binds specifically to terminal sialic acid residues in human transferrin, the second receptor being bound to a marker or having the ability to bind thereto, and the complex comprising the first receptor, human transferrin and the second receptor is determined by means of the marker.

DETAILED DESCRIPTION

It is generally preferable, in keeping with familiar and time-tested technology, to use an anti-transferrin antibody as the first receptor. It is of advantage if the first receptor is a polyclonal anti-transferrin antibody. Antibodies of this kind are commercially available (eg, Sigma, No. T2027). However, there are other receptors specific to human transferrin which are suitable too, provided they do not significantly impair the binding of the second receptor to the sialic acid residues. It would be conceivable, for example, to use human transferrin receptor.

The second receptor is preferably a lectin, the most preferred of which is the lectin Sambucus nigra; its production has been described by Brokert et al. (Biochem. J. 221, 103–109 (1984)).

According to one embodiment of the method of the invention, the first receptor is bound to a solid phase, as a result of which, during incubation, the transferrin becomes attached to the solid phase. According to another embodiment, however, the first receptor can also be present in solution; in this case the receptor is able to bind to a solid phase by means of a specific pair of binding agents, one of which is bound to the solid phase and the other to the receptor. Suitable pairs of binding agents are known to those versed in the art.

It is expedient to use a wall of a reaction vessel, such as a sample tube, a microplate or a cuvette as solid phase. The solid phase can also consist of a particulate material such as polystyrene or magnetic beads.

In the same way, the second receptor can either be bound directly to the marker or else be capable of binding thereto by way of a specific pair of binding agents. According to a preferred embodiment, the specific binding agents are biotin and streptavidin or avidin, with the second receptor typically carrying the biotin and the marker the streptavidin/avidin.

The sample fluid is incubated with the first receptor and the second receptor for a period of 10 to 60 minutes in each case, preferably 20 to 40 minutes, and at a temperature of 10 to 40° C. A 30-minute incubation period at room temperature provides good results.

Basically, all detection techniques commonly used in connection with immunoassays are suitable for determining the marker on the second receptor. Persons versed in the art are familiar with such techniques, and they do not need to be explained in detail here. They include, in particular, enzymatic techniques, ie, techniques in which the marker is an enzyme which is quantified by determining a substrate. Enzymes commonly used for such purposes include, eg, phosphatases such as alkaline phosphatase, oxidases, peroxidases, dehydrogenases such as glucose-6-deghydrogenase, hydrolases such as urease, etc. The enzymatic reaction typically generates a chromogenic, luminescent or fluorescent substrate, which can then be determined using a suitable method, usually a photometric method. Suitable chromogens include, eg, ABTS (2,2'-azino-bis-(3-ethyl)-benzthiazolin-6-sulfonic acid), orthophenyldiamine, tetramethylbenzidene, 5-amino-salicyclic acid, etc. Enzymatic techniques also encompass, eg, modifications to chemical or physical parameters—such as light absorption—which are caused by the substrate reaction. This means that the sialic acid residues can also be determined by UV methods with alcohol dehydrogenase, glucose-6-dehydrogenase etc, and by means of the coenzyme AND, NADP etc, or by using a diaphorase in the presence of NADP and the chromogen iodonitrotetrazolium violet in order to obtain a colored formazan derivative.

Besides enzyme markers, there are naturally other methods of marking the second receptor, eg, through use of fluorescent or luminescent tracers, or of radiotracers; radioactive labelling, however, is not recommended for practical reasons. Immunofluorescence tests can be carried out, eg, using a conjugate of the second receptor with IFTC (fluorescin isothiocyanate).

As sample fluid containing the transferrin to be determined, use is generally made of a body fluid such as blood, serum, urine, liquor, vitreous humor, bile, abdominal fluid, etc. If necessary, use is made of a body fluid which has been modified by chemical or physical treatment but which, however, is preferably free of anticoagulants. It is preferable if whole blood or serum is used as body fluid.

The subject matter of the invention also includes a method of determining sialicacid-deficient transferrin in body fluids, characterized in that (a) A sample of body fluid is assayed using a method according to one of the preceding claims, (b) the terminal sialic acid residues are determined for at least one standard which contains a defined quantity of a substance comprising sialic acid residues capable of binding to the second receptor, and (c) the content of sialic-acid-deficient transferrin is ascertained on the basis of the results obtained in step (a) and step (b).

It is preferable if step (b), ie, determination of sialic acid residues using known formulations, is repeated several times, each time with the standard containing a different quantity of sialic acid residues capable of binding to the second receptor. It is especially beneficial if three to seven, most preferably five to six measurements are carried out on different standards, and a calibration curve plotted from the results obtained. By comparing the readings obtained for the sample fluid with the calibration curve, the content of sialic-acid-deficient transferrin can be determined with a high level of accuracy.

As is obvious to a person versed in the art, it is a good idea to determine suitable negative and/or positive reference samples at the same time.

According to one embodiment, a standard is used which contains transferrin with a defined quantity of sialic acid residues. By this, one understands body fluids, especially pooled body fluids, and suitably formulated compositions. Suitable concentrations of sialic acid residues in the standards used to plot the calibration curve range from 0 to 50 $\mu$mol/dl, preferably from 2.5 to 25 $\mu$mol/dl.

In another embodiment, the standard contains a substance other than transferrin, with a defined quantity of sialic acid residues capable of binding to the second receptor. Examples of such substances are immobilized mucin and/or an immobilized oligosaccharide with a defined quantity of sialic acid residues capable of binding to the second receptor, eg, a mucin which is obtainable from Sigma (Sigma No. M 3895, mucin from bovine submaxillary glands). In this specification, the terms "immobilized" and "immobilizable" are used in the sense of "being bound to" and "being capable of binding to" the solid phase.

Another example is N-acetylneuramine-lacto-N-neotetraose c ($\alpha$Neu 5 AC-(2-6)-$\beta$Gal-(1-4)-$\beta$GlcNAc-(1-3)-$\beta$Gal-(1-4)-Glc (Sigma No. A4814) combined with a solid phase coated with concavalin A (Sigma No. C7275) (specific for $\alpha$-D-glycosyl bonds).

In cases where a fluid containing transferrin is used as standard, the transferrin is attached to the solid phase by means of the first receptor. Where a standard that contains a substance other than transferrin is used, it is not possible to attach the marker by means of a complex comprising the first receptor and transferrin, as will be obvious to a person versed in the art. In this case, the substance containing the sialic acid residues is accordingly immobilized, ie, is bound to a solid phase or is capable of binding thereto.

The method of the invention can be used to determine SDT in samples of body fluids from male and female donors. In the literature, healthy persons are reported as having a physiological transferrin content of 260 mg/dl±15%. Surprisingly, the method of the invention also provides accurate results for pregnant women.

According to an additional aspect, the invention also relates to the use of a lectin, especially the lectin Sambucus nigra, in a process for determining sialic-acid deficient transferrin.

Since sialic-acid deficient transferrin is a reliable marker for alcoholism, as was mentioned at the beginning, the method of the invention can considerably facilitate the diagnosis of alcohol abuse.

The subject matter of the invention thus also includes a method, eg, use of the aforementioned process, of diagnosing alcohol abuse or addiction. To this end, sialic-acid deficient transferrin is determined in a sample of body fluid and then compared with normal levels to see whether there is a pathological discrepancy in the number of terminal sialic acid residues. Comparison is carried out in the usual way, eg, using reference samples taken from patients and/or healthy persons. Alternatively, or in addition, it is also possible to calculate whether the measured level is within the normal range or not.

Further applications in this connection include, eg, the early recognition of regular alcohol abuse and alcoholism, monitoring therapeutic treatment of withdrawal patients, use as a differential-diagnostic instrument to distinguish between diseases induced by alcohol (eg. liver) and those of non-alcoholic origin, a laboratory-diagnostic aid in deciding on the start of pharmacoprophylaxis in intensive medicine, and generally in occupational and forensic medicine, eg, for providing expert opinions.

According to yet another aspect, the invention also relates to a reagents kit suitable for determining the terminal sialic acid residues in transferrin. A kit of this kind comprises an immobilized first receptor which binds specifically to human transferrin and, physically separated therefrom, a second receptor which carries a marker or is capable of binding to a marker and which binds specifically to terminal sialic acid residues in human transferrin, and also, if necessary, a solid phase which is capable of binding specifically to the first receptor, a marker which is capable of binding specifically to the second receptor, a substrate for the marker, and the customary adjuvants, buffers and additives.

The first receptor is preferably an anti-transferrin antibody, in particular a polyclonal anti-transferrin antibody, and the second receptor is preferably a lectin, in particular the lectin *Sambuca nigra*.

The reagents kit may contain, in addition, at least one standard which contains a defined quantity of a substance comprising sialic acid residues capable of binding to the second receptor, as was described before. This substance is preferably N-acetyineuramine-lacto-N-neo-tetraose c (αNeu 5 AC-(2-6)-βGal-(1-4)-βGlcNAc-(1-3)-βGal-(1-4)-Glc (Sigma No. A4814) which is capable of binding to a solid phase coated with concavalin A (Sigma No. C7275), or a mucin with a defined quantity of α-anomeric (2-6) sialic acid residues (eg, Sigma No. M3895, mucin from bovine submaxillary glands).

Yet another part of this invention's subject matter is a test strip for the qualitative and semi-quantitative determination of SDT, comprising (a) a sample application zone,
(b) at least one reaction zone, containing a first receptor which can be immobilized on a solid phase and which binds specifically to human transferrin, and a marked second receptor which binds specifically to terminal sialic acid residues in human transferrin, and
(c) a detection zone for immobilizing the first receptor, said zone containing a substance which binds specifically to said first receptor.

Test strips of this sort are known to persons skilled in the art, making a detailed description unnecessary. Briefly, a strip of this kind consists of a material through which a sample fluid containing a substance to be determined can migrate, eg, by capillary force or gravity, and which is inert with respect to the substance to be determined. After the fluid has been applied to the sample application zone, it migrates through a reaction zone, with ternary complexes of the first receptor, transferrin and the second, marked receptor being formed. These are subsequently immobilized in the detection zone. Non-bound reactants and substances migrate right through the detection zone and are collected in an end zone.

The first receptor is preferably an anti-transferrin antibody, in particular a polyclonal anti-transferrin antibody. The first receptor is preferably immobilized by means of biotin and streptavidin/avidin. The second receptor is preferably a lectin, in particular the lectin *Sambucus nigra*. Markers for the second receptor which are suitable for use in such test strips are known to persons versed in the art and include, eg, gold and silver markers and chromogens.

According to a particularly preferred embodiment, the test strip also includes at least one reference zone for negative and/or positive referencing. A negative referencing zone corresponds for the most part with the detection zone, except that there is no binding partner to immobilize the first receptor. A positive reference zone expediently contains a defined quantity of immobilized sialic acid residues which are capable of binding to the second receptor. For a semi-quantitative assay, a number of positive reference zones can be provided which have different amounts of sialic acid residues. Other test strip variants and layouts are described in the prior art.

The method of the invention can also be used to determine terminal sialic acid residues in all natural proteins which have siatic acid residues bound in the 2-6 position to β-galactose and N-acetyl glucosamine.

The method of the invention is explained in more detail by means of the following examples, together with FIGS. 1 and 2.

DETAILED DESCRIPTION OF THE PREFERRED EMBODIMENTS

Figure 1:
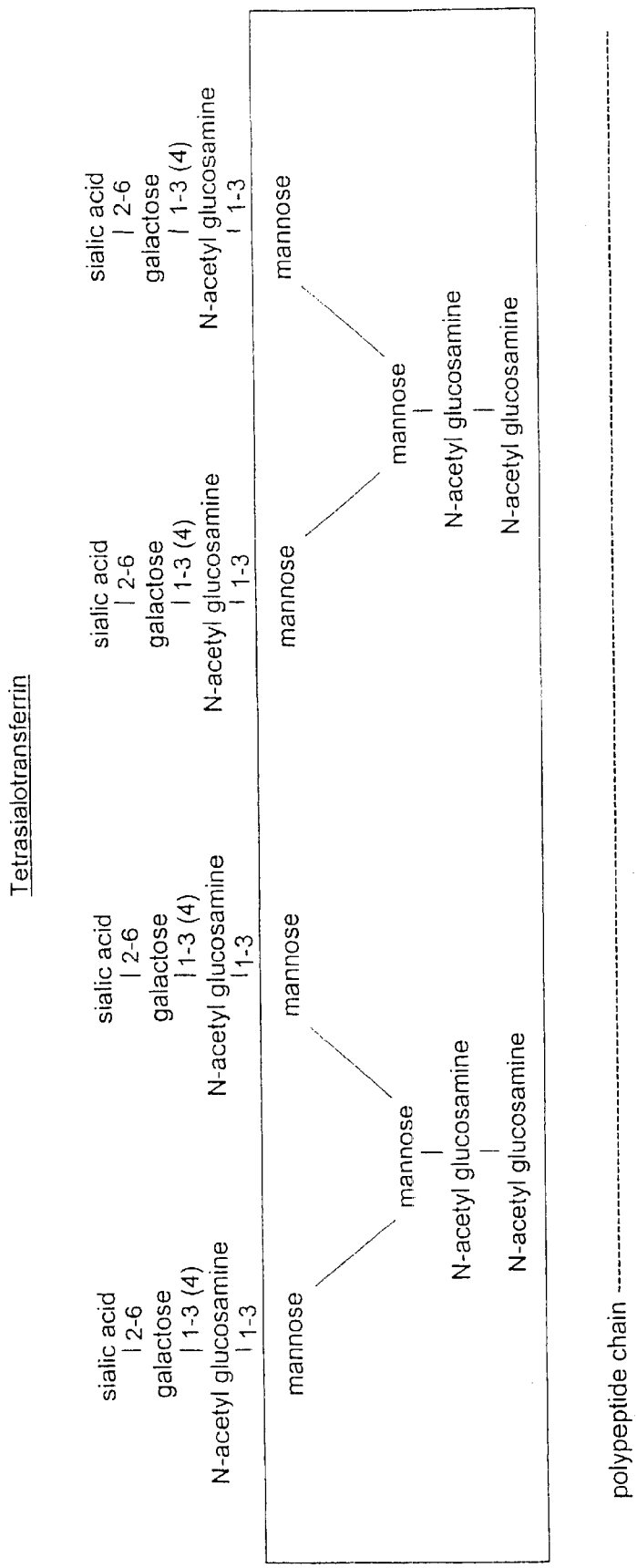
FIG. 1 is a schematic representation of glycosylation in the most common tetrasialotransferrin isomer. The terminal carbohydrate residues are sialic acid residues or acetyl sialic acid residues which are bound in the α2-6 position to galactose, the galactose, in turn, being bound to N-acetyl glucosamine.
Figure 2:
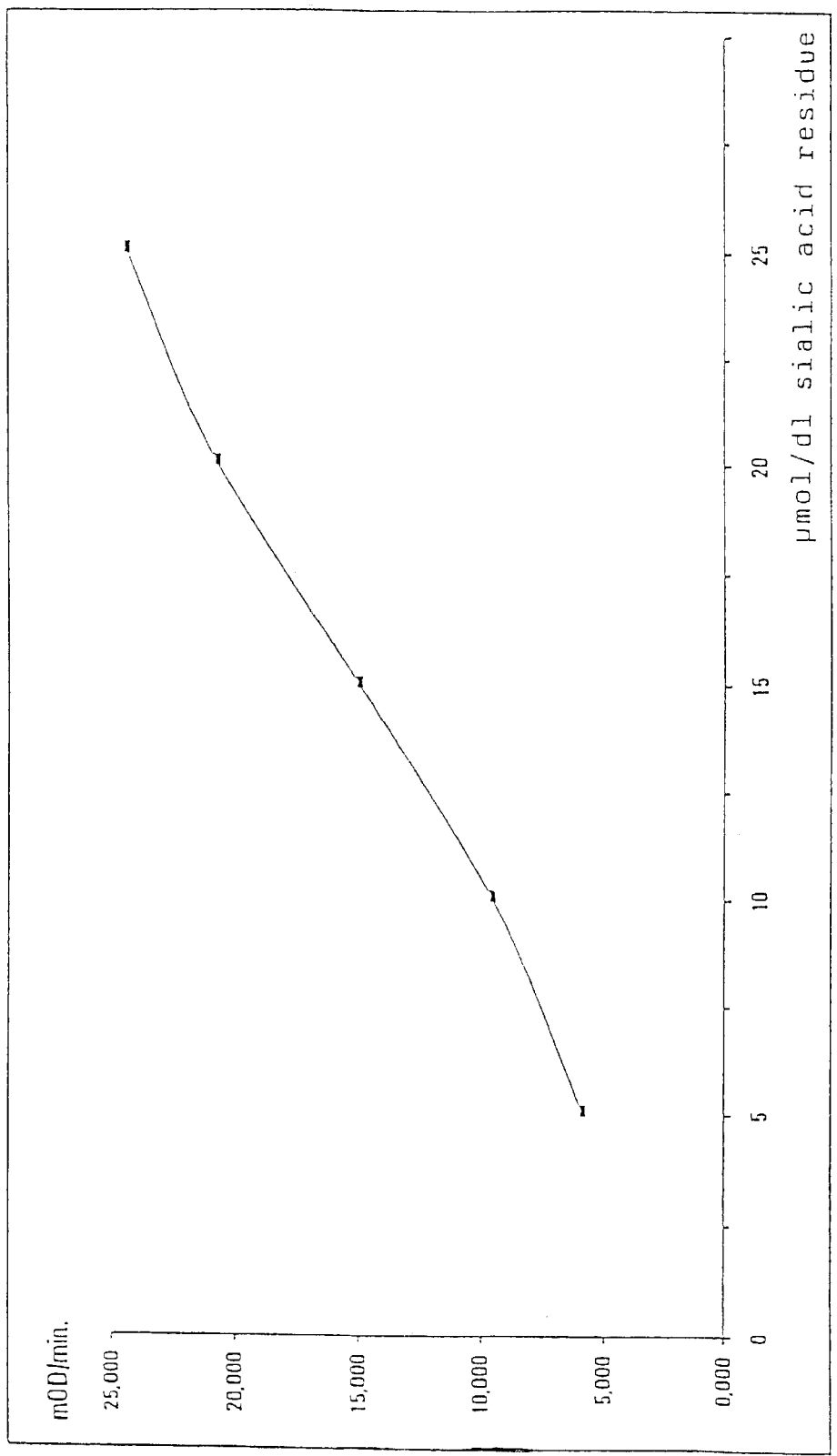
FIG. 2 shows a standard curve suitable for evaluating an SDT determination carried out according to the invention. As can be seen, the curve is a plot of the readings obtained for standards with 5 10, 15, 20 and 25 μmol/dl SAR (sialic acid residue).

The advantages of the new method are:

1. A high degree of specificity, since the lectin Sambucus nigra has a strong affinity for terminal α- anomeric sialic acids bound in 2-6 position.
2. High sensitivity (from up to 5 ng in the test).
3. Very good reproducibility.
4. Very high serial and day-to-day accuracy.
5. Unlike assaying methods used so far, which require complicated apparatus and experienced personnel, this fully immuno-enzymatic process is a neat and direct assaying method which does not require any time-consuming physicochemical separation processes for preparing the samples. It is thus a lot simpler, more readily available, very quick to carry out, and not liable to be affected by working errors during the sample preparation stage.
6. The great simplicity of the test, which can be used without any problem as a semi-quantitative test that can be read off with the naked eye and does not necessitate use of a photometer.

7. A very short reaction time of less than 2 hours for 96 assays per microplate.

EXAMPLES

The EIA method, two variants of which are described, is characterized by use of the specific lectin Sambucus nigra, which has a strong affinity for terminal (α-anomeric sialic acid residues bound in 2-6 position to the galactose-N-acetyl-glucosamine chain.

Quantification of these sialic acid residues ensues in three stages:

1. Formation of an antigen-antibody complex between the transferrin and a polyclonal anti-transferrin antibody which is bound to the microplate.
2. Formation of an additional molecular specific complex between peroxidase-labelled Sambucus nigra lectin and the sialic acid residues of the transferrin.
3. Oxidation of a chromogen (ABTS) in the presence of a substrate specific for peroxidase, the color intensity being proportional to the content of sialic acid contained in the transferrin molecule and being measured at 405 nm.

Example 1

Quantitative determination of sialic acid residues in human isotransferrins (SDT=sialic acid deficient transferrin) by means of an immunolectin-enzymatic reaction using a Sambucus nigra lectin conjugate.

a) Reaction Principle

During the first stage, the transferrin is separated from the other serum proteins by binding to a human anti-transferrin antibody which is attached to the surface of the microplate.

During the second stage, the sialic acid residues bound to the terminal oligosaccharide chains of the transferrin form a stable complex with the peroxidase-labelled Sambucus nigra lectin.

Subsequently, as a result of the action of a substrate specific for peroxidase on the chromogen ABTS in the presence of peroxidase, a green-blue color develops, the intensity of which is proportional to the content of sialic acid residues in the test.

b) Necessary Reagents

Serum diluent: PBS buffer: 0.01 M; pH 7.2–7.4; 0.05% Tween$^{20}$ and 1% albumin (BSA)

Wash solution: PBS buffer: 0.01 M; pH 7.2–7.4;

Sambucus nigra-lectin-peroxidase conjugate (commercially available from MEDAC No. H6801)

Citrate buffer solution substrate 0.12 M citrate solution, pH 4.0; 0.05% $H_2O_2$ (Peridrol)

ABTS substrate solution Citrate buffer solution, containing 1.5% ABTS (2,2' azino-bis-(3-ethyl)-benzthiazolin-6-sulfonic acid)

Stop solution Aqueous 1% sodium dodecylsulfate solution

Coated microplate with anti-transferrin antibodies (human anti-transferrin antibodies from the host animal, whole serum (Sigma No. T2027)

c) Preparation of the Microplates c1) Preparation of the anti-transferrin antibodies Add 2 ml of saturated ammonium sulfate solution [$(NH_4)_2SO_4$, MW 132.14, 900 g/l bidist. $H_2O$] dropwise to 4 ml of anti-transferrin antibody serum and stir with a glass rod.

Leave to stand for 60 min at 4° C.

Centrifuge for 15 min at 4° C.

Discard supernatant and resuspend the precipitate in 2 ml of PBS buffer (0.01 M; pH 7.2–7.4); repeat the last two steps four times.

Resuspend the final precipitate in 1 ml of PBS buffer and introduce into a dialyzing unit (dialyzing membrane: Serva, Heidelberg, dialysis tubing No. 20/32, order-No. 44110).

Dialyze at 4° C. against PBS buffer solution which must be renewed every two hours until it reacts negatively with Nessler's reagent (Nessler's reagent for ammonium salts, Merck No. 1.09028)

Then determine the protein concentration of the purified anti-transferrin antibody by means of the Biuret reaction (required concentration approximately 20–50 mg/ml). c2) Coating the Plate The polystyrene microplates are coated with 100 $\mu$l of the highly purified polyclonal anti-transferrin antibody (lgG) solution. For coating the microplate, the final concentration of the solution should be 20 mg protein/ml in carbonate buffer solution (0.1 M, pH 9.6). The coating is applied by incubating passively for 24 hours at 4° C., without an agitator. The plates are rinsed three times with the wash solution and stored at minus 20° C.

d) Preparing the Test Serum

The sera are diluted 1/10 with the diluent (100 $\mu$l+900 $\mu$l).

e) Preparing the Standards and References

The serum standards containing 25, 20, 25, 10, 5, 2.5 $\mu$mol SAR/dl (SAR=sialic acid residues) and the reference serum containing 20 $\mu$mol SAR/dl are reconstituted with 0.5 ml of bidistilled water.

f) Application of Samples, Standards and References

It is recommended that one perform duplicate assays for each test. Pipette 100$\mu$l portions of each prepared solution into the microplate wells. For the blank reading, pipette 100 $\mu$l of diluent into each of two wells. Incubate for 30 min at room temperature, agitating the microplate.

After three consecutive washes (always begin with the blanks!) the damp plate is tapped carefully on absorbent paper.

g) Application of the Sambucus Nigra Lectin Conjugate

Introduce 100 $\mu$l of conjugate solution into the microplate wells and incubate for 30 min at room temperature, agitating the plate. The specific conjugate forms a stable complex with the sialic acid residues that are bound along with the transferrin/antitransferrin. After three consecutive washes as before, the damp plate is tapped carefully on absorbent paper.

h) Application of the Substrate and the Chromogen

Introduce 100 $\mu$l ABTS substrate solution into the microplate wells and incubate for 10 min at room temperature, agitating the plate. The reaction ensues with a green-blue coloration of the oxidized chromogen.

Kinetic measurement of this reaction comprises 3 point-readings at 5—minute intervals following the initial 10—minute incubation period. The reaction can be stopped for an end-point reading after 30 min by adding 50 $\mu$l of stop solution (1% SDS). Alternatively, the end-point reading can simply be taken after 30 minutes of incubation.

i) Measurement at 405 nm using a microplate photometer j) Evaluation

The reading are evaluated by means of a conversion curve that must be plotted:

1. Logarithmic Standard Curve

Using the following formula, the extinction differences obtained for the standards are plotted as common logarithms against the common-logarithmic standard concentrations:

$$\text{Log} \cdot \Delta E_{min} = \log \cdot \mu\text{mol/dl } SAR$$

2. Sigmoid Standard Curve

Using the following formula, the extinction differences obtained for the standards are plotted as common logarithms against the common-logarithmic standard concentrations:

$$\text{Log} \cdot \Delta E = \frac{(a-d)}{[1+(x/c)^b]} + d \ \mu\text{mol/dl } SAR$$

The reference serum with 20 μmol SAR/dl should result in extinction differences in the following ranges:

0.276±10% after 15' (0.248–0.304)

0.426±10% after 30' (0.383–0.492)

0.528±10% after 60' (=.475–0.581)

Example 2

Example 1 was repeated, except that instead of the Sambucus nigra lectin—peroxidase conjugate use was made of biotinylated Sambucus nigra lectin—(MEDAC, No. BA 6801) and a streptavidin-peroxidase conjugate.

To this end, in step g), pipette 100 μl of a solution of biotinylated lectin into the microplate wells, incubate for 30 min at room temperature while agitating the plate and then, after washing three times, pipette 100 μl of streptavidin-peroxidase conjugate solution into each well, incubate again for 30 min at room temperature while agitating the plate, and wash three times as before.

The reference serum with 20 μmol SAR/dl should result in extinction differences in the following ranges:

0.353±10% after 15' (0.318–0.388)

0.546±10% after 30' (0.491–0.601)

0.572±10% after 60' (0.515–0.629)

Example 3

Preparation of a Transferrin-free Standard

Materials

Lectin concavalin A (Con A) from Canavalia ensiformis tack bean) (Sigma No. C7275)

N-acetyineuramine-lacto-N-neo-tetraose c (αNeu 5 AC-(2-6)-βGal-(14)-βGlcNAc-(1-3)-βGal-(1-4)-Glc, sodium salt, from human milk, MW: 1020.9 g/mol (Sigma No. A4814).

Following saturation of lectin Con A (specific for α-D-glycosyl bonds) by means of sialic acid residues in different concentrations (6—point calibration), a microplate is coated with the saturated lectin, or complex. Binding of Sambucus nigra lectin and reaction with the substrate ensues as is described in Example 1, steps g) and h).

Alternatively, transferrin-free standard may be prepared by first immobilizing an excess of lectin Con A on the microplate. The sialic acid residues in concentrations of 200, 100, 50, 25, 12.5 and 6.5 20 μmol SAR/l are added by pipette to the immobilized lectin.

Example 4

Comparison

For healthy men and healthy non-pregnant women, a physiological transferrin content of 260 mg/dl (221–299 mg/dl) is quoted in the literature. Based on molecular weights of 77,000 g/mol for transferrin and 308.3 g/mol for SAR, and assuming an average of 5 SAR per transferrin molecule, an SAR concentration is calculated in the range from about 14.35 μmol/dl to 19.42 μmol/dl.

The average SAR content in serum from a healthy reference group was found to be 50.51 μmol SAR/g transferrin (Stibler et al., Clinical and Experimental Research, Vol. 10,, No. 1, Jan/Feb. 1986). Assuming a relative deviation of ±15% from the theoretical transferrin concentration (about 260 mg/dl), the following ranges result for the concentration of 50.51 μmol SAR/g found by Stibler et al.:

|  | Low range | High range |
| --- | --- | --- |
| μmol SAR/g transferrin | 42.94 | 58.08 |
| μmol SAR/dl | 12.83 | 17.36 |
| Calculated according to the invention (see above) | 14.35 | 19.42 |
| Measured | 14.18 | 19.33 |

These results show that the quantification of transferrin using the method of the invention leads to results which agree well with calculated levels and those quoted in the literature.

The above quantification was carried out according to the method of Example 1. As standard, use was made of mucin with a given content of α-anomeric (2-6) sialic acid residues (Sigma No. M3895, mucin from bovine submaxillary glands) in concentrations of 25, 20, 15, 10, 5 and 2.5 μmol SAR/dl.

What is claimed is:

1. A method for determining sialic acid deficient human transferrin in a body fluid sample, comprising the steps of
   incubating a body fluid sample with a first receptor which binds specifically to human transferrin to form a first complex;
   separating the thus formed first complex from the body fluid sample; incubating the first complex with *Sambucus nigra* lectin which binds specifically to terminal sialic acid residues in human transferrin, said *Sambucus nigra* lectin being bound to a marker to form a second complex formed of the first receptor, human transferrin and lectin;
   determining a value for the second complex by detecting said marker;
   determining a value of terminal sialic acid residues in at least one standard solution which comprises a defined quantity of at least one immobilized oligosaccharide and which binds to said *Sambucus nigra* lectin by adding an amount of said *Sambucus nigra* lectin to said standard solution and determining binding of said *Sambucus nigra* lectin to sialic acid residues in said standard solution; and
   comparing values of sialic acid residues obtained in said body fluid sample and said standard solution to determine sialic acid residues in said body fluid sample; wherein said oligosaceharide is N-acetylneuramine-lacto-N-neo-tetraose c which binds to a solid coated with concanavalin A.

2. The method of claim 1, wherein sialic acid residues in from three to seven standard solutions are determined, each of which contains a different quantity of sialic acid residues which bind to the *Sambucus nigra* lectin.

3. The method of claim 1, wherein said at least one standard solution further comprises transferrin with a defined quantity of sialic acid residues.

4. The method of claim 1, wherein said at least one standard solution further comprises a substance other than transferrin and N-acetylneuramine-lacto-N-neo-tetraose c which binds to a solid coated with concanavalin A having a defined quantity of sialic acid residues.

5. The method of claim 4, wherein said substance is selected from the group consisting of an immobilized mucin or an immobilized oligosaccharide which has a defined quantity of sialic acid residues which bind to the *Sambucus nigra* lectin.

6. The method of claim 1, further comprising determining alcohol abuse by said subject by comparing the value of said sample to a normal level found in a non-alcoholic subject.

7. The method of claim 1, wherein said body fluid sample is taken from a subject undergoing therapeutic treatment for alcohol withdrawal, said method further comprising determining efficacy of therapeutic treatment by determining sialic acid deficient human transerrin in said body fluid sample.

8. The method of claim 1, wherein said body fluid sample is taken from a subject with a disease, said method further comprising determining whether said disease is induced by alcohol.

9. The method of claim 1, in wherein said first receptor is an anti-transferrin antibody.

10. The method of claim 9, wherein said antibody is a polyclonal antibody.

11. The method of claim 1, wherein the first receptor is bound or binds to a solid phase, said method further comprising incubating or separating one of the first and second complexes in presence of the solid phase.

12. The method of claim 11, wherein said solid phase is a wall of a reaction vessel, a sample tube, a microplate, a cuvette, or particulate material.

13. The method of claim 1, wherein the lectin is biotinylated and the marker is coupled with avidin or streptavidin.

14. The method of claim 1, wherein the marker is an enzyme.

15. The method of claim 14, wherein the enzyme is a peroxidase, alcohol dehydrogenase, glucose-6-dehydrogenase, or diaphorase.

16. The method of claim 1, wherein the marker is a fluorescent or luminescent marker.

17. The method of claim 1, wherein the human body fluid is serum or whole blood.

\* \* \* \* \*